United States Patent
Stoianovici et al.

(10) Patent No.: US 7,021,173 B2
(45) Date of Patent: Apr. 4, 2006

(54) REMOTE CENTER OF MOTION ROBOTIC SYSTEM AND METHOD

(75) Inventors: Dan Stoianovici, Baltimore, MD (US); Louis L. Whitcomb, Baltimore, MD (US); Dumitru Mazilu, Baltimore, MD (US); Russell H. Taylor, Severna Park, MD (US); Louis R. Kavoussi, Lotherville, MD (US)

(73) Assignee: The John Hopkins University, Baltimore, MD (US)

( * ) Notice: Subject to any disclaimer, the term of this patent is extended or adjusted under 35 U.S.C. 154(b) by 193 days.

(21) Appl. No.: 10/359,284

(22) Filed: Feb. 6, 2003

(65) Prior Publication Data

US 2003/0221504 A1 Dec. 4, 2003

Related U.S. Application Data

(60) Provisional application No. 60/354,656, filed on Feb. 6, 2002.

(51) Int. Cl.
*B25J 17/00* (2006.01)

(52) U.S. Cl. ............................. 74/490.05; 74/490.03; 901/16; 901/23; 901/30

(58) Field of Classification Search ............ 74/490.01, 74/490.03, 490.05; 901/16, 23, 30; 414/744.1
See application file for complete search history.

(56) References Cited

U.S. PATENT DOCUMENTS

| | | | |
|---|---|---|---|
| 4,068,763 A | 1/1978 | Fltecher et al. | .......... 214/1 CM |
| 4,098,001 A | 7/1978 | Watson | |
| 4,149,278 A | 4/1979 | Wiker et al. | .................. 3/12.5 |
| 4,355,469 A | 10/1982 | Nevins et al. | |
| 4,409,736 A | 10/1983 | Seltzer | |
| 4,477,975 A | 10/1984 | De Fazio et al. | |
| 4,501,522 A | 2/1985 | Causer et al. | .................. 414/4 |
| 4,537,557 A | 8/1985 | Whitney | |
| 4,556,203 A | 12/1985 | Rourke et al. | |
| 4,666,361 A | 5/1987 | Kitabatake et al. | .......... 414/380 |

(Continued)

*Primary Examiner*—David Fenstermacher
(74) *Attorney, Agent, or Firm*—Arent Fox PLLC (57) ABSTRACT

A remote center of motion robotic system including a base unit and a plurality of linking units. The base unit is rotatable about a first axis. The plurality of linking units are coupled with one another. At least two of the linking units are kept parallel to each another during motion. The plurality of linking units are coupled with that base unit at a first end. The plurality of linking units are rotatable about a second axis by changing an angle between each of the plurality of links.

27 Claims, 7 Drawing Sheets

Kinematic Principle

U.S. PATENT DOCUMENTS

| | | | |
|---|---|---|---|
| 4,970,448 A | 11/1990 | Torii et al. | 318/568.1 |
| 5,207,114 A * | 5/1993 | Salisbury et al. | 74/479.01 |
| 5,305,653 A * | 4/1994 | Ohtani et al. | 74/490.03 |
| 5,397,323 A | 3/1995 | Taylor et al. | |
| 5,515,478 A | 5/1996 | Wang | |
| 5,630,431 A | 5/1997 | Taylor | |
| 5,647,554 A * | 7/1997 | Ikegami et al. | 242/390.9 |
| 5,792,135 A * | 8/1998 | Madhani et al. | 606/1 |
| 5,817,084 A | 10/1998 | Jensen | |
| 5,876,325 A | 3/1999 | Mizuno et al. | |
| 5,907,664 A | 5/1999 | Wang et al. | |
| 6,047,610 A | 4/2000 | Stocco et al. | |
| 6,105,454 A | 8/2000 | Bacchi et al. | 74/490.03 |
| 6,246,200 B1 | 6/2001 | Blumenkranz et al. | 318/568.11 |
| 6,267,022 B1 * | 7/2001 | Suzuki | 74/490.01 |
| 6,408,224 B1 * | 6/2002 | Okamoto et al. | 700/245 |
| 6,558,107 B1 * | 5/2003 | Okuno | 414/744.5 |
| 6,675,671 B1 * | 1/2004 | Jokiel et al. | 74/490.09 |
| 6,889,119 B1 * | 5/2005 | Riff et al. | 700/254 |

\* cited by examiner

Figure 4: Kinematic Principle

Fig. 5a

SECTION A-A  Fig. 5b

Figure 5: Frontal View and Central Cross Section of the Module at $\beta = 0°$ and $\gamma = 0°$ Figure 6: Top View and Aligned Cross Section of the Module at $\beta = 0°$ and $\gamma = 7.5°$

FIG.7

REMOTE CENTER OF MOTION ROBOTIC SYSTEM AND METHOD

CROSS REFERENCE TO RELATED APPLICATION

This application claims priority to provisional patent application no. 60/354,656, entitled ADJUSTABLE REMOTE CENTER OF MOTION ROBOTIC MODULE, filed on Feb. 6, 2002, the contents of which are incorporated herein by reference.

BACKGROUND OF THE INVENTION

1. Field of the Invention

The present invention relates to robotic devices and methods. In particular, the invention relates to systems and methods for orienting an end-effector about two axes intersecting at a fixed geometric point located distally, materializing a pivot point or a Remote Center of Motion (RCM).

2. Description of the Related Art

In robotics the pivot point and kinematic principle used is commonly referred to as the Remote Center of Motion. Systems and methods for orienting parts, tools, and instruments about a RCM point distal to the mechanism are well known. For example, see U.S. Pat. Nos. 5,397,323, 5,515,478, 5,630,431, 5,817,084, 5,907,664, 6,047,610, and 6,246,200, the entire contents of each are incorporated herein by reference.

The RCM principle is commonly used in freehand surgical practice. In robotic assisted surgery, several mechanisms implementing the RCM principle have also been developed. The present invention is a new type of RCM mechanism possessing unlimited rotations, with no kinematic singularities, and adjustable RCM point.

U.S. Pat. No. 4,098,001 to Watson introduced the precursor of the RCM, the Remote Center of Compliance (RCC) principle, which was derived for industrial robot applications of peg-in-hole insertions. RCC mechanisms give rotational and translational compliance for the "peg" at the insertion point into the "hole" so that the robot can perform the assembly operation in case of misalignment. Commonly, the motion is restricted to a narrow region and it is passive.

U.S. Pat. No. 4,098,001 describes a passive 3-D n-bar linkage RCC mechanism for part assembly operations. A flurry of inventions by Watson's collaborators (see U.S. Pat. Nos. 4,409,736, 4,477,975, 4,556,203, and 4,537,557; Nevins J, (1981): "Systems analysis and experimental study advance the art of assembly automation", Assembly Automation, vol. 1, no.4 p. 186–9; Masamune K, Patriciu A, Stoianovici D, Susil R, Taylor R E, Fichtinger G, Kavoussi L R, Anderson J, Sakurna I, Dohi T, (1999), "Development of CT-PAKY frame system—CT image guided Needle puncturing manipulator and a single slice registration for urological surgery", Proc. 8th annual meeting of JSCAS, Kyoto 1999:89–90) describe a number of other solutions employ rigid and elastic linkage mechanisms, both passive and active, to achieve RCC motion for manufacturing assembly operations. All of these mechanisms have limited range of angular motion as a result of their linkage designs. Currently, numerous passive types of 3-D linkage RCC devices are commercially available, for example from ATI Industrial Automation (http://www.ati-la.com/another.htm), RISTEC (http://wyvw.ristec.com/rcc.htm), and PFA, Inc. (http://www.pfa-inc.com/rccfront.html). The RCC mechanism only allows rotational, pivoting motion about the fulcrum point, it is performed on a larger range, and it is normally actuated.

U.S. Pat. No. 5,397,323 to Taylor et al. introduced the RCM principle with the invention of the "Remote Center-of-Motion Robot for Surgery". The invention was implemented on an LABS robot developed at IBM, which uses a pivot RCM point proximal to the patient but distal from the robotic mechanism. See also U.S. Pat. No. 5,630,431. In the Taylor systems, the first axis of rotation points into the RCM, and the second axis is materialized by a parallelogram mechanism implemented by two coupled parallel linkages of rigid bars and cylindrical joints. The two axes of the RCM are orthogonal, and the mechanism operated around an upright initial (zero) direction.

In U.S. Pat. No. 5,630,431, the robot uses two concentric goniometer arcs of normal relative orientation connected in series. See also Cutting C B, Bookstein F L, Taylor R H, (1996): "Applications of Simulation, Morphometrics and Robotics in Craniofacial Surgery, in Computer-Integrated Surgery," MIT Press 1996: Cambridge, Mass. p. 641–662; 37. Taylor R E, (1991): "A Model-Based Optimal Planning and Execution System with Active Sensing and Passive Manipulation for Augmentation of Human Precision in Computer-integrated Surgery", Second Int. Symposium on Experimental Robotics, Toulouse, France; Taylor R H, (1992): "Augmentation of Human Precision in Computer-Integrated Surgery", Innovation et Technologie en Biologie et Medicine, 13(4 (special issue on computer assisted surgery)): p. 450–459; and Taylor R H., (1992): "A Passive/Active Manipulation System for Surgical Augmentation", First Int. Workshop on Mechatronics in Medicine, Malaga, Spain. The RCM point is located at the common center of the guides, which is located distal from the mechanism. The two directions of rotation are orthogonal. The location of the pivot point is locked by the architecture of the mechanism, and the robot could only be operated around an upright initial orientation.

In 1998, Jensen modified Taylor's initial design in U.S. Pat. No. 5,817,084. The robot in that patent replaced the parallel linkage of bars at the base of the parallelogram mechanism with a belt drive ("Flexible Drive"). The mechanism was implemented on an SRI robot for laparoscopy. See Cornum R L, Bowersox J C: Telepresence: a 21st century interface for urologic surgery. J Urol. 1996; 155 (Supp 5): 489A. Abstract 715. Although Jensen realized the advantage of replacing the parallel linkage with a continuous transmission, he did not fully eliminate its use. For this reason, his mechanism inherited certain poor characteristics of the Taylor system: limited range of motion around an upward zero, unequal stiffness at different positions. This prior art RCM system is also unadjustable and has axes that are orthogonal.

It is known that the RCM point can be defined and mechanically locked by the kinematics of the mechanism, or can be arbitrarily chosen and implemented with a high degrees-of-freedom (DOF) mechanism under coordinated joint control. Almost any high mobility robot can be programmed to perform such a task. U.S. Pat. No. 6,047,610 describes an example. This approach has advantages of pivot flexibility, increased maneuverability, and overall versatility. However, these mechanisms are unsafe for surgical applications. Mechanical RCMs are safer due to their reduced DOF, decoupled motion and locked pivot features.

Between 1996 and 1999 Wang et al. reported a series of ten inventions entitled "Automated Endoscope System for Optimal Positioning" [42,43] or similar for the AESOP robot (Computer Motion, Inc., Goleta, Calif., http://www.compumotermotion.com/). The last two joints of the AESOP robot are passive and rotary with intersecting axes. The intersection of these axes is neither remote from the mechanism nor located at the laparoscopic port level. The laparoscopic instrument occupies a free orientation between the end of the robot and the laparoscopic entry port. The AESOP is not a genuine RCM mechanism, but rather, a floating RCM, which provides a safe way of pivoting the laparoscope.

More recent advancements in the RCM field are related to the daVinci robot (Intuitive Surgical, Inc., Mountain View, Calif., http://www.intusurg.com/). See U.S. Pat. No. 6,246, 200. This system comprises a bilateral surgical robot and a camera holder performing laparoscopic tasks under direct control of a surgeon located at a command console. Both the robot and the surgeon's console use a version of an RCM mechanism. The RCM mechanism is a very elegant, but rather massive version of the original Taylor RCM. Like Jensen, Intuitive Surgical modified the base linkage of the parallelogram mechanism in order to accommodate the drive-of the additional cable driven DOF. Kinematically, daVinci has the same capabilities as Taylor's LARS robot.

With very few exceptions, the prior art RCM mechanical devices for use in surgical applications are either goniometer arc systems or are variations on the Taylor design, from the original LARS robot to the newest and highly sophisticated daVinci. The prior art devices each have limitations that beg improvement. In particular, rigid linkage RCM designs have limited range of motion.

Thus, there is a need for new and improved image based target guiding systems and methods that take advantage of commonly available imaging technology and solve the problems with the prior art.

SUMMARY OF THE INVENTION

According to an embodiment of the present invention, an "uncalibrated" system and method are provided for accurate needle placement without precise camera/imager calibration.

According to an embodiment of the present invention, a robotic module is provided that can be used to orient an end-effector about two axes intersecting at a fixed geometric point located distal to the mechanism materializing a pivot point or a Remote Center of Motion (RCM). A robotic tool (or end-effector) mounted on an RCM module will rotate about the RCM point, which can be conveniently located on the end-effector since this point is remote from the robotic module.

The module presents two rotational degrees-of-freedom (DOF) with coincident axes at the geometric RCM point. The position of the pivot is adjustable along one axis by modifying the relative angle between the axes. As such, the two rotations are not necessarily orthogonal.

Unlike all previous RCM mechanisms, which all possess kinematic singularity points, this new mechanism provides unrestricted rotation about both axes with no singularities. This is achieved by using a double belt-drive not previously reported. It also allows the end-effector to rotate about any initial orientation of the mechanism, folded, extended, or midway. The mechanism presents uniform mechanical properties at different orientations. Mechanical and/or electronic means can used to limit and set the desired range of motion.

The present invention is a new RCM device for performing controlled motion in the form of a robotic module. The novelty of this device is that it can attain any rotational orientation without encountering the kinematic singularities that limit the motion of all previously reported mechanisms of rigid linkage RCM designs. With special end-effector adapters the module can manipulate various tools/instruments. The module can be used standalone or in conjunction with other robotic components for increased DOF. It also provides an RCM motion without any part of the mechanism impinging "over" the center of motion (i.e., without the mechanism interfering with free access from the RCM point along a direction orthogonal to the two rotational axes of the RCM mechanism.

According to an embodiment of the present invention, a remote center of motion robotic system is provided. The system includes a base unit and a plurality of linking units. The base unit is rotatable about a first axis. The plurality of linking units are coupled with one another. At least two of the plurality of linking units remain parallel to each another throughout motion. The plurality of linking units are coupled with the base unit at a first end. The plurality of linking units are rotatable about a second axis by changing an angle between each of said plurality of links.

According to an embodiment of the present invention, a remote center of motion robotic system is provided. The system includes a base means for rotating about a first axis. The system also includes a plurality of linking means for rotating about a second axis by changing an angle between each of the plurality of linking means. The plurality of linking means are coupled with the base means at a first end.

BRIEF DESCRIPTION OF THE DRAWINGS

The objects and features of the invention will be more readily understood with reference to the following description and the attached drawings, wherein.

DETAILED DESCRIPTION OF THE PREFERRED EMBODIMENTS

The present invention provides a novel apparatus and method for performing image assisted surgery. The invention includes a robotic system or module that can be used to orient an end-effector about two axes intersecting at a fixed geometric point, located distal to the mechanism materializing a pivot point, referred to herein as a Remote Center of Motion (RCM). An end-effector, for example, a robotic tool such as a needle driver, may be mounted upon an RCM module and configured to rotate about the RCM point, which can be conveniently located on the end-effector since this point is remote from the robotic module.

The present invention is configured to allow two rotational degrees-of-freedom (DOF) with coincident axes at the geometric RCM point. The position of the pivot is adjustable along one axis by modifying the relative angle between the axes, referred to herein as the adjustment angle. As such, the two rotations are not necessarily orthogonal.

Unlike prior art RCM mechanisms, which possess kinematic singularity points, the present invention provides a double belt-drive configuration that helps achieve unrestricted rotation about both axes with no singularity points. The present invention also allows the end-effector to rotate about any initial orientation of the RCM mechanism, including folded, extended, or any orientation in between. The present invention is capable of uniform mechanical properties at different orientations. Mechanical and/or electronic means can used to limit and set the desired range of motion.

Figure 1A:
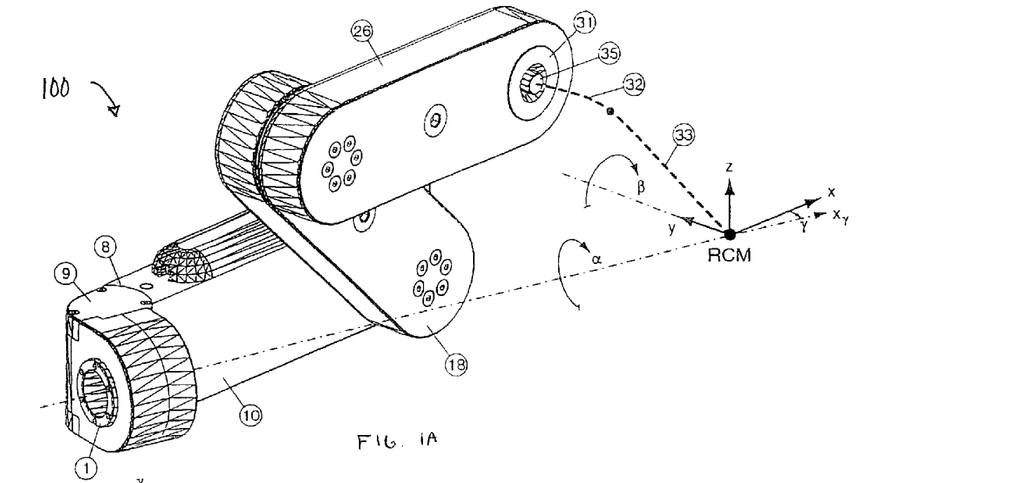
FIGS. 1A–1C are diagrams of the robotic module according to an embodiment of the present invention.
Figure 1B:
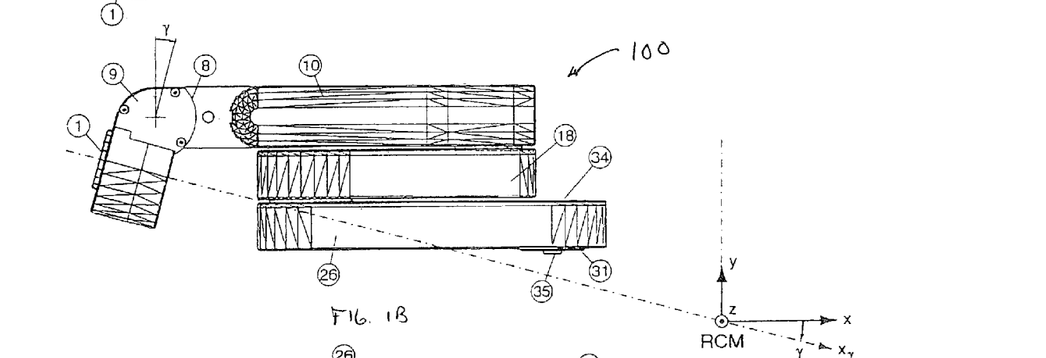
Figure 1C:
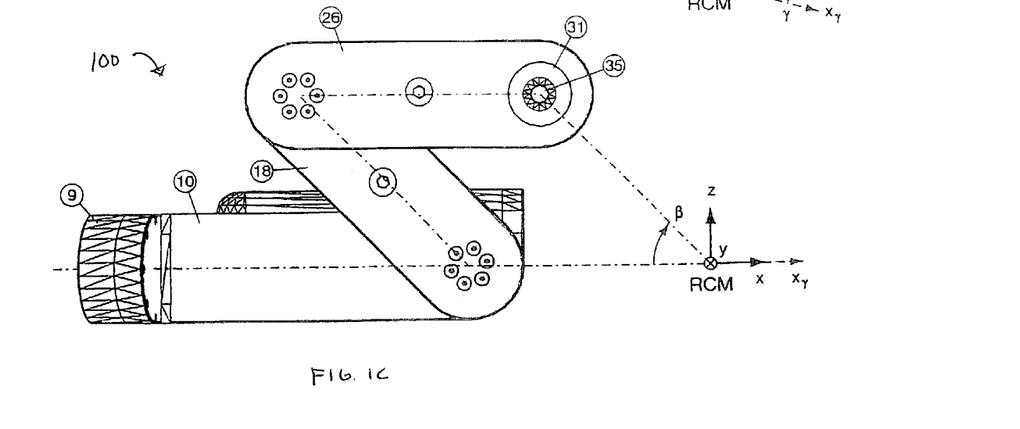

FIGS. 1A–1C show an isometric, top, and frontal view, respectively, of an RCM module according to an embodiment of the present invention. The module or mechanism 100 includes first, second and third arms (also referred to as links and linking units) 10, 18, and 26, respectively. First arm 10 is coupled with a base element 9, which can be secured to a base, such as a fixed support or a forerunner robotic component, through the base shaft 1. Third arm 26 is configured to receive a holder/driver 32 that holds an end-effector 33, which can be connected on either side of the output shaft 31 or 34 of arm 26. A mounting screw 35 is used which can accommodate different end-effectors for different applications. The means for coupling the each of the elements are described below in more detail.

The system 100 is configured to allow two active DOF: a) rotation $\alpha$ about axis $x_\gamma$ of the base shaft 1 representing a first pivoting axis; and b) rotation $\beta$ about axis y of the parallelogram structure formed by arms 18, 26, and end-effector (32–33), representing a second pivoting axis y. The two axes intersect at the center of the xyz coordinate system, representing the pivot point or RCM point of the mechanism.

System 100 is configured so that the adjustment angle $\gamma$ between the elements 9 and 10 can be adjusted, and the elements 9 and 10 can be locked in a desired relative orientation. The adjustment angle $\gamma$ changes the orientation of the axis $x_\gamma$ and shifts the location of the RCM point along the second pivot axis y. This angular adjustment design allows for conveniently setting the pivot point to accommodate different end-effectors while maintaining a compact design. One drawback is the degeneration of the orthogonal pivoting axes (x & y|$\gamma$=0) into the non-orthogonal pivot ($x_\gamma$ & y|$\gamma$>0). This reduces the working envelope and, if necessary, requires coordinated motion of the axes to obtain an orthogonal pivoting motion of the end-effector. Nevertheless, for small adjustment angles the degeneracy is minimal. During testing, when the adjustment angle $\gamma$ {0°, 15°}, no difficulties were found related to this issue.

The second pivoting axis y is materialized by the pseudo-parallelogram mechanism described by the links 18, 26, and the end-effector 33/holder 32. The link 18 may be actuated with respect to link 10, and the link 26 maintains its parallel orientation with respect to link 10. The end-effector 33/holder 32 (which is rigidly attached to the output shaft 31, 34) maintains its relative orientation with respect to link 18. Output shaft 31, 34 is rotatable, and therefore, the orientation of end-effector 33/holder 32 with respect to link 26 is adjustable.

This design allows for rotating the end-effector 33/holder 32 about an axis y, which is remote from the mechanism. In fact this is the classic RCM design. The novelty of the present module is given by the kinematic design and mechanisms used to implement the parallelogram.

The two pivot axes have unlimited motion, and the axes are able to continuously spin. This is not necessarily important for performing multiple turns, but is important for allowing different operation modes. The initial (zero) position of the mechanism 100 can be set at any angle, especially at any $\beta$ angle, and can allow the end-effector to pivot from one side to the other of that zero-set direction in space. FIGS. 2A–2B and 3A–3B illustrate two examples respectively.

Figure 2A:
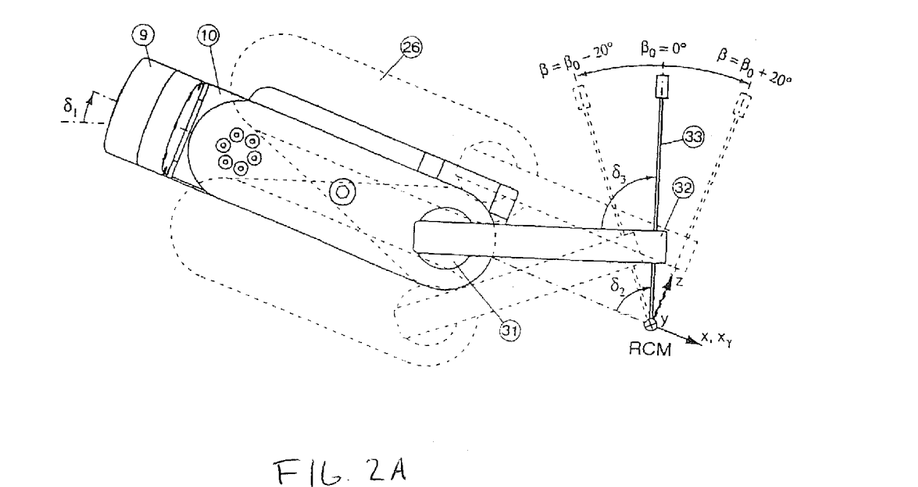
FIGS. 2a and 2B are schematic representations of the module in FIGS. 1a–1c, according to an embodiment of the present invention.
Figure 2B:
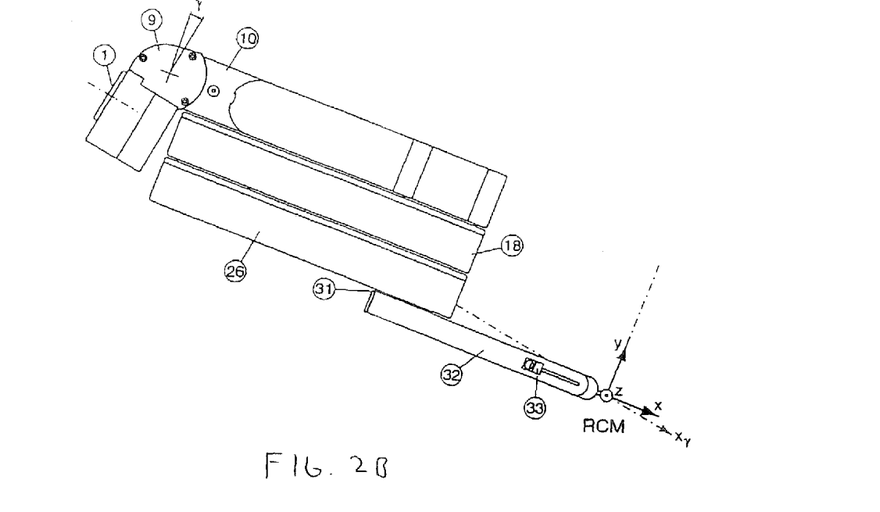

Operating about a "Folded" initial position, $\beta_0$=0°: FIGS. 2a–2b respectively show a frontal view of the module and its top, aligned view together with a special end-effector 33 and holder 32. The mechanism 100 oriented at $\beta$=$\beta_0$=0° is represented with solid lines, and it pivots about a "folded" position of the module, are exemplified by the two dotted positions $\beta$=$\beta_0$±20°.

The mechanism 100 is shown as mounted inclined ($\delta_1$>0°) with respect to the ground in order to raise the mechanism above the RCM point. The holder 32 supports the end-effector 33 at an angle $\delta_3$=90°, and the end-effector is positioned at $\delta_2$=$\delta_3$–$\delta_1$ with respect to the mechanism, so that in the initial position $\beta$=$\beta_0$=0°, the end-effector 33 is vertical.

The holder 32 is shown as connected on the outer side 31 of the module. An adjustment of the adjustment angle $\gamma$>0° is used to shift the RCM point along the y axis and place it at the tip of the end-effector 33. Thus, the RCM is the pivot point for the $x_\gamma$ & y|$\gamma$>0 axes.

This folded operation mode ($\beta_0$=0°) allows the module not just to clear the RCM pivot, but also to clear the region above the RCM. This is important in performing image-guided procedures, wherein the robot should be distal from the active field of the image to allow unimpeded visualization of the target and end-effector during the procedure.

Figure 3A:
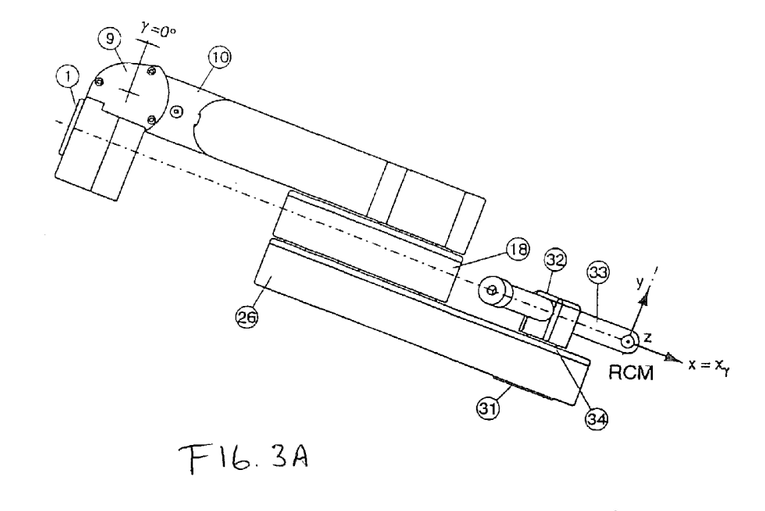
FIGS. 3A and 3B are schematic representations of the module in FIGS. 1a–1c, according to an embodiment of the present invention.
Figure 3B:
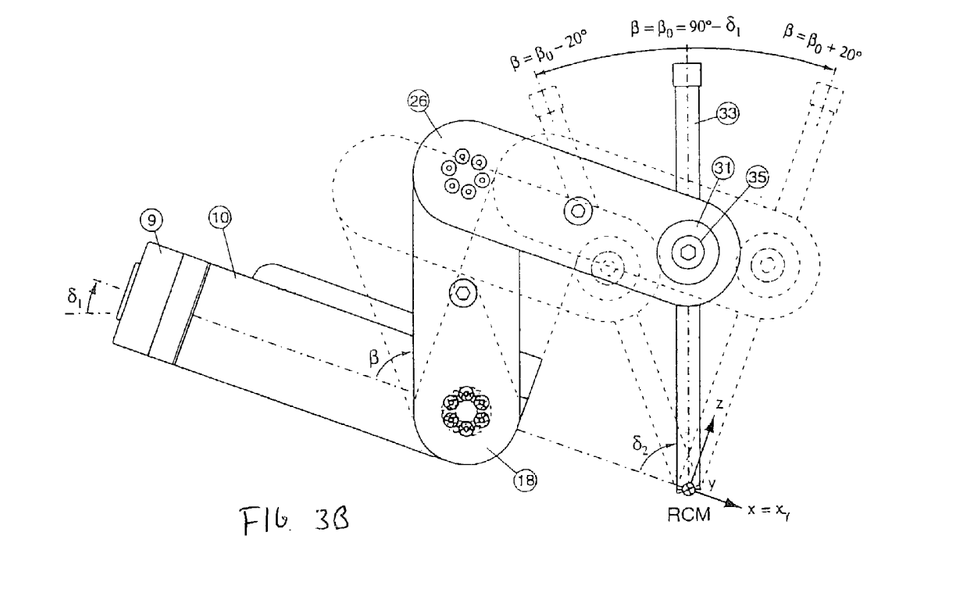

FIGS. 3A–3B illustrate an example wherein the mechanism is pivoting about an "unfolded" position $\beta$=$\beta_0$Z=90°. As for the folded case, the mechanism is inclined ($\delta_1$>0°) with respect to the ground in order to lower the RCM point. The end-effector 33, however, is mounted along the holder ($\delta_3$=0°, see FIG. 3A) and passes through the axis of the output shaft 31 and 34 so that $\delta_2$=$\beta$ (see FIG. 3B). In this case, the initial orientation is chosen to place the end-effector 33 vertically at an angle $\beta_0$=90°–$\delta_1$. Moreover, it is possible to construct the holder 32 so that the pivot directions are orthogonal ($\gamma$=0°) by connecting it on the opposite (inner) side 34 of the module. In the case that the end-effector 33 interferes with the link 18 for very small $\beta$ angles, the outer mounting, which avoids interference, could also be employed. This unfolded mode with $\beta_0$ near 90° is suitable for situations when the presence of the robotic module above the RCM pivot does not encumber the operation, in procedures such as robotically assisted laparoscopy.

Accordingly, the module can operate about a folded ($\beta$=0°), normal ($\beta$=90°), inverted ($\beta$=–90°), extended ($\beta$=180°), or any unfolded position ($\beta${–90°, 0°, 90°, 180°}), with end-effector 33 mounting on either side of the mechanism. The folded and unfolded operation modes exemplified above are two preferred arrangements of initial positions, orientation of the module, holder design, and side mountings showing the large variety of potential architectures and application capabilities.

Figure 4:
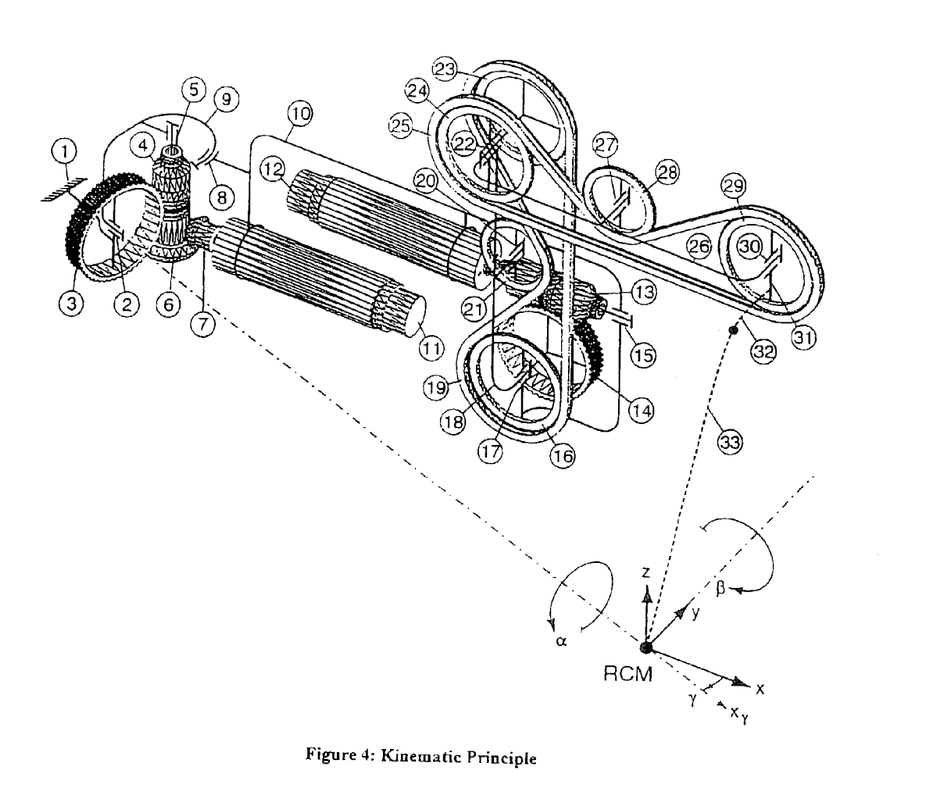
FIG. 4 is a schematic of the kinematic principals of the module in FIGS. 1A–1C, according to an embodiment of the present invention.

FIG. 4 illustrates the kinematic design of the RCM module according to an embodiment of the present invention. Six links (1, 9, 10, 18, 26, 31) and five revolute joints (2, 8, 17, 22, 30) are shown. One of these joints is passive ($\gamma$ adjustment 8) and three other joints (17, 22, 30) are kinematically coupled by belts, so that the mechanism presents only two active DOF (2,17-22-30).

Module 100 incorporates three main mechanisms: the base adjustment angle, the first pivoting joint of rotation a along the inclined direction $x_\gamma$, and the pseudo-parallelogram mechanism.

The base adjustment angle is realized by changing the angle between the elements 9 and 10 of module 100, which are coupled by the joint 8. A convex and respectively a concave cylindrical shape can be mated to implement the revolute joint 8, which can be set and locked at the desired orientation.

The first pivoting joint of rotation a along the inclined direction $x_\gamma$ is implemented by the revolute joint 2 acting between the input shaft 1 and the link 9. In the preferred embodiment, this joint is activated by a worm transmission 3–4 by mounting worm gear 3 on the input shaft 1. The worm transmission may be a Bail-Worm type described in U.S. Provisional Patent Application 60/339,247, entitled "Miniature Ball-Worm Transmission", filed on Oct. 16, 2002, which is incorporated herein by reference.

A bevel gear transmission 6–7 is used to actuate the worm 4 from the actuator motor 11 of the first axis. These components are arranged so that the adjustment joint 8, the worm 4, and the bevel gear 6 are coaxial. The worm 4 and the bevel gear 6 are rigidly attached to one another and supported by a set of bearings 5 located at the center of convex joint surface of 9. This kinematic chain insures that the motion of the actuator motor 11 is transmitted to the output shaft 1 at any set position $\gamma$ of the adjustment joint 8. In this way the actuator motor 11 could be compactly located in the base link 10, together with the actuator motor 12 of the other pivoting axis.

The pseudo-parallelogram mechanism is implemented by the remaining components. For clarity, FIG. 4 shows the module for a $\beta=90°$ angle of the second pivot axis. The parallelogram (more easily observed in the frontal views of FIG. 1C and FIG. 3B) is formed between the links 18, 26, and the holder 32 and/or end-effector 33. An imaginary line connects the output shaft 31 to the RCM pivot. Three joints of this parallelogram are 17, 22, and 30, and the fourth one is imaginary representing the second RCM pivot. In the RCM prototype, the parallelogram has equal sides of 100 mm. The only actuated joint is 17 and the other two are coupled to it through belt-drive mechanisms of 1:1 non-slip transmission ratios implemented by the two belts 19 and 25 (timing belt, chain, cable chain, cable drive, metallic belts, etc.).

The revolute joint 17 acting between links 10 and 18 is engaged by the worm mechanism 13–14, actuated by the motor 12 mounted in the link 10, with the worm 13 supported by the set of bearings 15. Preferably, worm mechanism 13–14 is implemented by the mechanism described in provisional patent application 60/339,247.

An inverted-pulley mounting design can be used to generate the motion of a parallelogram mechanism with two belt-drives rather than a classic four-bar linkage. In this case, the motor rotates the link 18 with angle $\beta$; the link 26 stays parallel to the base 10 at any rotation $\beta$; and the output shaft 31 maintains its orientation (stays parallel) with respect to link 18. For this, the gear 14 spins the link 18 and not the pulley 16, which is attached to the base element 10. Thus, the second pulley 23 of the first belt 19, tensioned by the idler 21 mounted on the bearing 20, maintains its orientation with respect to the base 10. A similar inverted-pulley mounting is then employed for the second 26 and third 31 edge of the parallelogram. Link 26 is attached through a shaft to the pulley 23, thus remaining parallel to base 10, and the first pulley 24 of the second belt 25 is connected to the previous link 18. The idler 21 supported by the bearing 20 tensions the belt 25, coupling the second pulley 29. In this way the output shaft 31, which is attached to the pulley 29 maintains its relative orientation with respect to link 18, closing the pseudo-parallelogram mechanism.

The combined kinematic design implements an adjustable pivot RCM mechanism of non-orthogonal $x_\gamma$ & y|$\gamma$>0 axes at the RCM point, which can operate around any $\beta$ angle (folded, normal, extended, inverted, or generally unfolded position), with bilateral end-effector mounting.

Figure 5A:
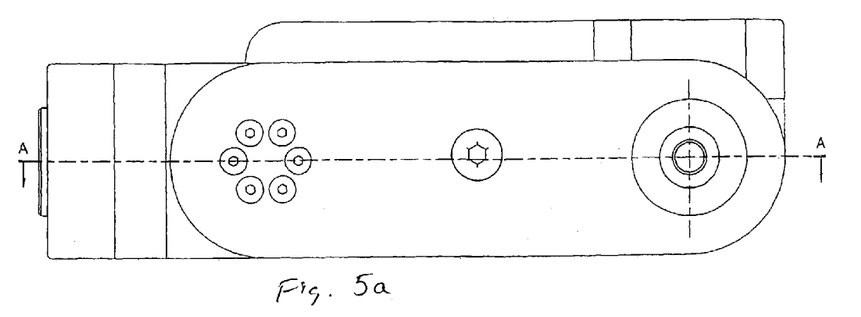
FIGS. 5A and 5B are a frontal view and a cross sectional view of the module in FIGS. 1A–1C, according to an embodiment of the present invention.
Figure 5B:
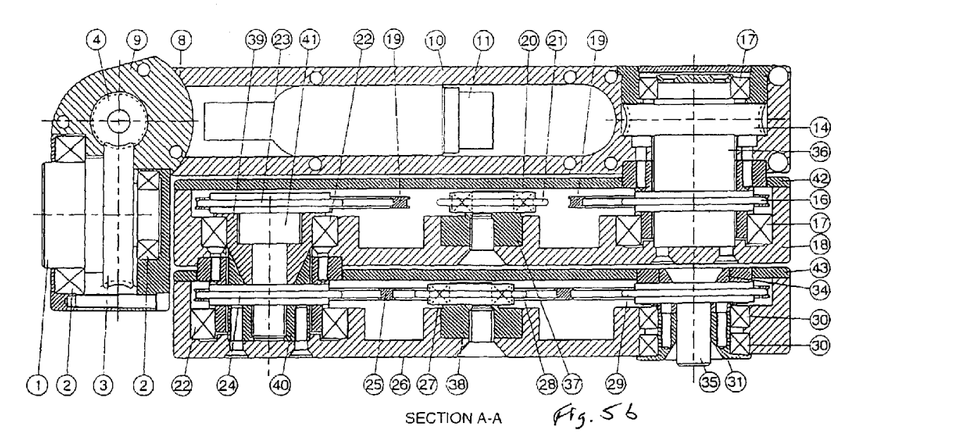

Certain mechanical aspects of the present invention are described with reference to FIGS. 5A–5B. FIGS. 5A–5B illustrate a frontal view and a central cross-section A—A of the RCM module 100 in its folded position ($\beta=0°$) and with an orthogonal pivot setup ($\gamma=0°$). The figure depicts an embodiment of the present invention using the Ball-Worm mechanisms.

For the Ball-Worm embodiment, the worm gears 3 and 14 have been machined on their shafts 1 and 35, respectively, as represented in the figure. In the classic worm embodiment, the worm gears have been mounted on the shafts by press fitting and securing with a longitudinal key.

The bearings used to implement the joints of the kinematic design (FIG. 4) are labeled with the same number in FIG. 5$b$. For example, the shaft 1 is supported by two bearings 2. The adjustment joint $\gamma$ of the base angle y between the links 9 and 10 can be easily observed in the cross-section A—A, as well as co-axially with the axis of the worm 4. The links 18 and 26 can be covered with thin lids 42 and 43, respectively.

FIG. 5B also depicts the inverted-pulley mounting of the belts 19 and 25. The pulley 16 is fixed with respect to the base 10 and the gear 14 engages the link 18. Similarly, the pulley 24 is mounted on link 18, and the pulley 23 engages link 26. The belts can be tensioned using idlers 21 and 28 mounted on the bearings 20 and 27 supported by the eccentric shafts 37 and 38, respectively, and locked by the flat head screws.

An angular adjustment at the level of the kinematic joint 22 has been incorporated for adjusting the angle between links 18 and 26 in the assembly process so that link 26 is parallel to the base link 10. This allows for mounting the pulleys on their shafts in any initial orientation, for tensioning of the belts, and performance of the "timing" of the belts. This mechanism allows for adjusting the angle between the pulley 23 and link 26 and locking it in the desired orientation. For this, the pulley 23 is mounted on a shaft 39 presenting a conic surface mated the shaft 40, which is attached to the link 26. The adjustment is performed setting the relative angle between the shafts 39 and 40 and locking it with the screw 41.

The output shaft presents a symmetric construction so that the end-effector holder can be mounted on the conic surface of either side 31 or side 34 with the screw 35. FIG. 5B depicts the screw 35 mounted from the side 31 of the shaft 34 for attaching the holder on the side of the shaft 31 (outer side). For mounting on the opposite side (inner side) the screw 35 is reversed, with its head on the side 31 of the shaft.

Figure 6:
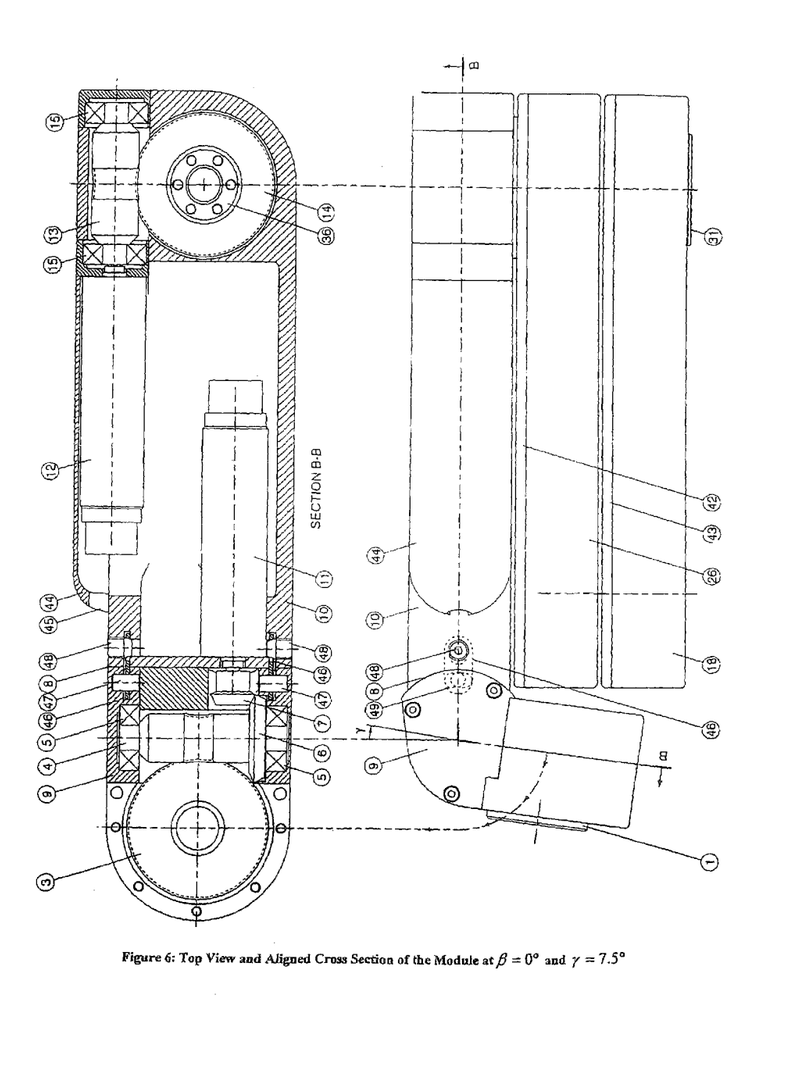
FIGS. 6A and 6B are a top view and an aligned cross sectional view of the module in FIGS. 1A–1C, according to an embodiment of the present invention.

FIGS. 6A and 6B present a top view of the module and an aligned cross section B—B through the center of the adjustment joint. The mechanism is represented at the middle of the base adjustment angle at $\gamma=7.5°$ and for a folded position of the mechanism $\beta=0°$.

FIG. 6B depicts the base adjustment arrangement and its bilateral tensioning mechanism, which comprises the plate 46, the dowel pin 47, and the setscrew 48 presenting a tapered point. The dowel pin 47 is inserted into the link 9 presenting a radial channel 49 coaxial with the adjustment joint 8. In this way, the pin 47 can sweep the channel adjusting its location so that the tensioning plate 46 maintains a normal direction at the surface of the joint 8. Thus, the plate 46 is secured at on end into the link 9 by pin 47. At the other end of the plate 46 is a hole, which is engaged on the conical part of the tapered setscrew 48, which is threaded into link 10. This acts like a wedge between the conical surface of 48 and the hole in plate 46, activated by the setscrew 48. By loosening the setscrews 48, on both sides of the link 10, the plate 46 is released unlocking the adjustment joint 8, and vice versa for locking.

FIG. 6B also shows the placement of both actuator motors 11 and 12 compactly into the body of link 10, and the motor cover 44 allowing immediate access to the motors. All electric components, motor connectors, and redundant encoder connections, which have been incorporated in the second prototype, are placed in the hollow space of link 10, next to the motors. The wiring cable is released through the hole 45 drilled in the cap 44.

According to an embodiment of the present invention, the RCM module can be a Ball-Worm RCM (BW-RCM), that is, a robotic module for surgical applications that implements a fulcrum point located 100 mm distal to the mechanism. The BW-RCM presents a compact design and can be folded into a small structure and can weigh very little (e.g., 175×68×54 mm structure at only 1.35 Kg). The BW-RCM can precisely orient a surgical instrument in space while maintaining the location of one of its points.

The kinematic architecture of the RCM module of the present invention makes it suitable for minimally invasive applications as well as trocar/needle orientation in percutaneous procedures. The RCM module of the present invention can accommodate various end-effectors. For example, the RCM may be used in conjunction with the Percutaneous-Access-of-the-Kidney (PAKY) radiolucent needle driver (See 26. Stoianovici D, Cadeddu J A, Demaree R D, Basile H A, Taylor R H, Whitcomb L L, Sharpe W N, Kavoussi L R: An Efficient Needle Injection Technique and Radiological Guidance Method for Percutaneous Procedures. *Lecture !Votes in Computer Science*, 1997 *CVRNIed-MRCAS'*, Springer-Verlag, 1997; 1205:295–298; Stoianovici D, Cadeddu J A, Demaree R D, Basile H A, Taylor R H, Whitcomb L L, Kavoussi L R: A Novel Mechanical Transmission Applied to Percutaneous Renal Access. *Proceedings of the ASME Dynamic Systems and Control Division*, 1997; DSC-61:401–406; and Stoianovici D, Kavoussi L R, Whitcomb L L, Taylor R H, Cadeddu J A, Basile H A, Demaree R D. (1996), "Friction Transmission with Axial Loading and a Radiolucent Surgical Needle Drive", Provisional U.S. patent of Invention No. 60/038,115. Filed as regular U.S. utility and PCT application on Feb. 20, 1998 by Johns Hopkins University. Pending U.S. patent application Ser. No. 09/026, 669 filed in Feb. 20,1998. Published PCT document WO 98/36688; the contents of each are incorporated herein by reference) for performing image-guided percutaneous renal access. The robot can orient and insert the needle using X-ray fluoroscopy guidance from a C-Arm imager as controlled by the surgeon. With the PAKY radiolucent needle driver the module operates around a folded position $\beta=0°$ thus clearing the x-ray field, and uses a base adjustment angle $\gamma=9.3°$ thus generating a non-orthogonal pivot. The system can be used for percutaneous renal access, offering an unquestionable improvement of needle placement accuracy and procedure time while reducing the radiation exposure to patient and urologist.

The RCM module of the present invention can be used with a special needle driver for computer topography (CT) registration. The Z-Stage PAKY is a modified version of the PAKY needle driver adapted to implement a CT/MRI registration method in addition to PAKY's needle driving capabilities, constructed in collaboration with the NSF Engineering Research Center for Computer Integrated Surgical Systems and Technology (CISST) at the Johns Hopkins University and the University of Tokyo [13, 1–6, 20]. As with the PAKY driver, the RCM also operates in a folded mode with non-orthogonal axes.

Figure 7:
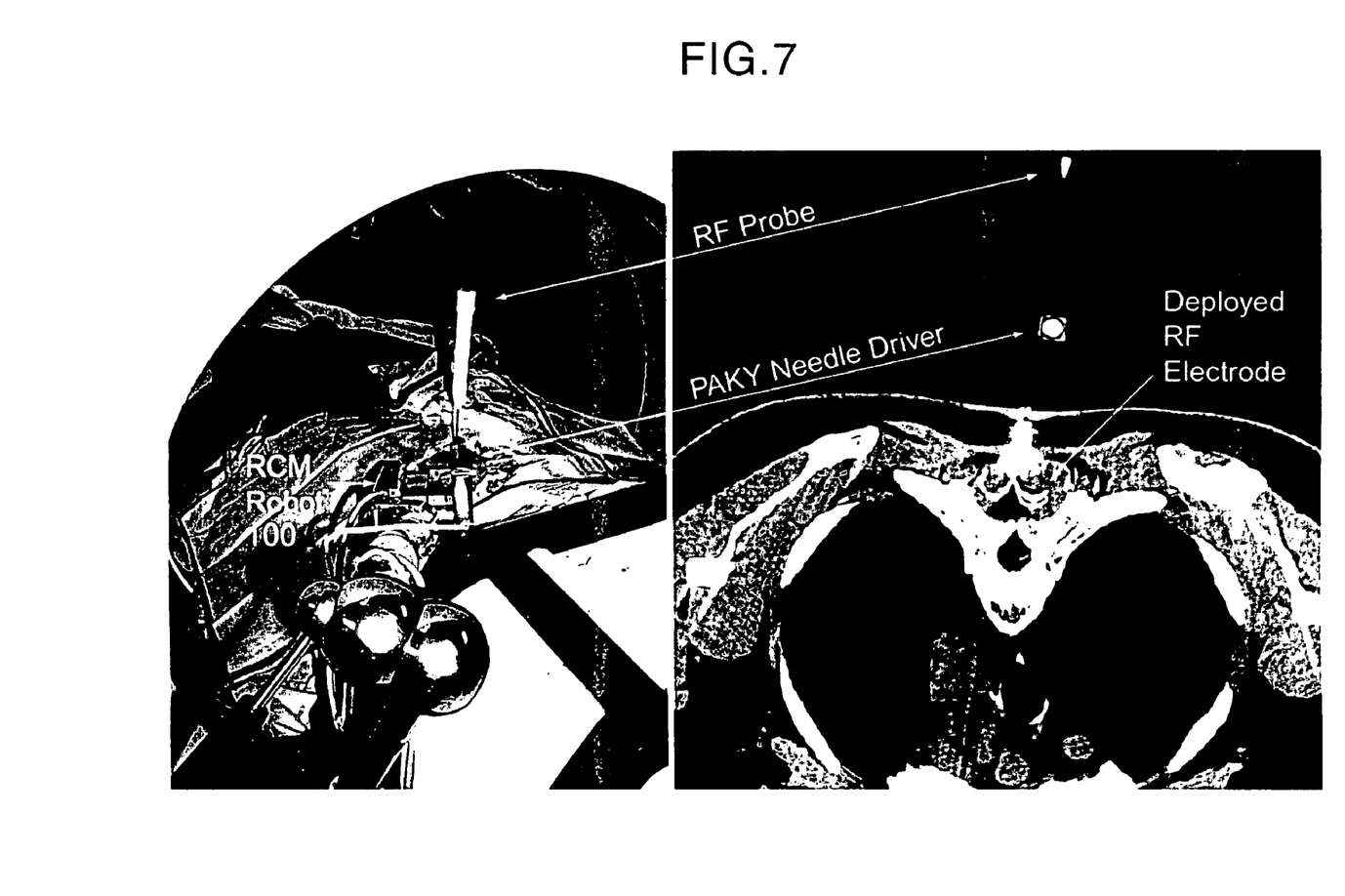
FIG. 7 shows an RCM module under CT guidance according to an embodiment of the present invention.

FIG. 7 shows that under CT guidance, the RCM module of the present invention can be used for kidney and spine percutaneous procedures using a simple method for robot registration in CT and MR imaging system. The method uses the laser markers readily available on any CT scanner and does not require imaging thus eliminating radiation exposure. Unlike the manual approach, the method allows for performing oblique insertions, for which the skin entry point and the target are located in different slices.

A high DOF robotic system incorporating the RCM has been developed in for CT guidance operations. FIG. 8 shows this system configured for CT-guided percutaneous renal access. As it can be observed in the picture, in this case the robot also presents a folded non-orthogonal operation mode ($\beta_0=0°$, $\gamma=9.3°$), but it is placed vertically for perineal access, presenting a base inclination angle (FIG. 2) of $\delta_1=90°$.

Accordingly, described above is an RCM module, which is a compact robotic module capable of orienting an end-effector in two directions in space about a pivot point located distal to the mechanism. Applications of the remote pivoting motion include industrial and, most importantly, surgical operations because this type of motion is commonly involved in manual surgical practice. The module accommodates various end-effectors and operation modes yielding application flexibility. The multiple clinical applications performed with multiple modular arrangements show the versatility of the RCM, its utility and safety for surgical use.

Thus, having fully described the invention by way of example with reference to the attached drawing figures, it will readily be appreciated that many changes and modifications may be made to the invention and to the embodiments disclosed without departing from the scope and spirit of the invention as defined by the appended claims.

We claim:

1. A remote center of motion robotic system comprising:
   a base link unit;
   a connecting link unit, the connecting link unit moveably coupled to the base link unit at a first rotating joint;
   the first rotating joint comprising a first round member and a first rotation axis, the connecting link unit rotates around the first rotation axis, and the first round member is coupled to the base link unit such that the angle of the first round member with respect to the base link unit is constant;
   an end link unit, the end link unit moveably coupled to the connecting link unit at a second rotating joint;
   the second rotating joint comprising a second round member, a third round member and a second rotation axis, the end link unit rotates around the second rotation axis, the second round member is coupled to the end link unit such that the angle of the second round member with respect to the end link unit is constant, the third round member is coupled to the connecting link unit such that the angle of the third round member with respect to the connecting link unit is constant, the first round member is coupled to the second round member so that the angle of the first round member with respect to the second round member is constant;

a base unit, the base unit comprising a base rotating joint; and the base rotating joint comprising a base unit round member moveably coupled to the base unit so that the base unit can rotate around a base axis, the base unit round member configured to couple the base unit to a base, wherein the base link unit is moveably coupled to the base unit at a pivot joint, the pivot joint having a pivot axis that is not parallel to the base axis.

2. The remote center of motion robotic system of claim 1, further comprising:
a base unit rotating motor drivingly coupled to the base rotating joint to rotate the base unit around the base axis.

3. The remote center of motion robotic system of claim 1, further comprising:
a connecting unit rotating motor drivingly coupled to the connecting link unit to rotate the connecting link unit around the first axis.

4. The remote center of motion robotic system of claim 3, further comprising a base unit rotating motor drivingly coupled to the base rotating joint by a first worm gear drive that rotates the base unit about the base axis to rotate the base unit around the base axis; and
wherein the connecting unit rotating motor is drivingly coupled to the connecting link unit with a second worm gear drive that rotates the connecting link unit about the first rotation axis.

5. The remote center of motion robotic system of claim 1, wherein the pivot axis and the base axis are orthogonal.

6. The remote center of motion robotic system of claim 1, wherein the first rotation axis and the pivot axis are orthogonal.

7. The remote center of motion robotic system of claim 1, wherein the pivot joint is a passive joint, said passive joint setting an adjustment angle of base axis from an X axis parallel to the base link unit.

8. The remote center of motion robotic system of claim 1, further comprising:
a third rotating joint, the third rotating joint is carried by the end link unit, the third rotating joint comprising a fourth round member that rotates around a third rotation axis, the third round member is coupled to the fourth round member so that the angle of the third round member with respect to the fourth round member is constant.

9. The remote center of motion robotic system of claim 8, further comprising:
an end-effector, the end-effector coupled to the end link unit at the third rotating joint, the end-effector coupled to the fourth round member so that the angle of the fourth round member with respect to the end-effector is constant.

10. The remote center of motion robotic system of claim 9, wherein
changing the angle between the base link unit and the connecting link unit allows an rcm end of the end-effector to rotate about a remote center of motion point.

11. The remote center of motion robotic system of claim 9, wherein the end-effector is coupled to the end link unit in a position parallel to the connecting link unit.

12. The remote center of motion robotic system of claim 8, wherein the first round member is coupled to the second round member with a first belt drive; and the third round member is coupled to the fourth round member with a second belt drive.

13. The remote center of motion robotic system of claim 8, further comprising:
a connecting unit rotating motor drivingly coupled to the connecting link unit to rotate the connecting link unit around the first axis.

14. The remote center of motion robotic system of claim 13, further comprising:
a base unit rotating motor drivingly coupled to the base rotating joint to rotate the base unit around the base axis.

15. A remote center of motion robotic system comprising:
a base unit, the base unit comprising a base rotating joint;
the base rotating joint comprising a base unit round member moveably coupled to the base unit so that the base unit can rotate around a base axis, the base unit round member configured to couple the base unit to a base;
a base unit rotating motor drivingly coupled to the base rotating joint to rotate the base unit around the base axis;
a base link unit, the base link unit moveably coupled to the base unit at a pivot joint, the pivot joint having a pivot axis that is not parallel to the base axis;
a connecting link unit, the connecting link unit moveably coupled to the base link unit at a first rotating joint;
the first rotating joint comprising a first round member and a first rotation axis, the connecting link unit rotates around the first rotation axis, and the first round member is coupled to the base link unit such that the angle of the first round member with respect to the base link unit is constant;
a connecting link rotating motor drivingly coupled to the connecting link unit to rotate the connecting link around the first rotation axis;
an end link unit, the end link unit moveably coupled to the connecting link unit at a second rotating joint;
the second rotating joint comprising a second round member, a third round member and a second rotation axis, the second and third round members rotate around the second rotation axis, the end link unit rotates around the second rotation axis, the second round member is coupled to the end link unit such that the angle of the second round member with respect to the end link unit is constant, the third round member is coupled to the connecting link unit such that the angle of the third round member with respect to the connecting link unit is constant, the first round member is coupled to the second round member so that the angle of the first round member with respect to the second round member is constant;
a third rotating joint, the third rotating joint is carried by the end link unit, the third rotating joint comprising a fourth round member that rotates around a third rotation axis, the third round member is coupled to the fourth round member so that the angle of the third round member with respect to the fourth round member is constant; and
an end-effector, the end-effector is coupled to the end link unit at the third rotating joint so that the angle of the fourth round member with respect to the end-effector is constant.

16. A remote center of motion robotic system comprising:
a base linking unit;
a connecting linking unit;
first rotating joint means for moveably connecting the base linking unit to the connecting linking unit;
an end linking unit;
a second rotating joint means for moveably connecting the connecting linking unit to the end linking unit;
kinematic means for kinematically connecting the first and second rotating joint means;
a base rotating joint means for coupling a base unit to a base; and
a pivot means for coupling the base unit to the base linking unit.

17. The remote center of motion robotic system of claim 16, further comprising:
a base unit rotating means coupled to the base rotating joint means for rotating the base unit around a base axis.

18. The remote center of motion robotic system of claim 16, further comprising:
a connecting unit rotating means coupled to connecting linking unit for rotating the connecting linking unit around a first axis.

19. The remote center of motion robotic system of claim 16, wherein the pivot means is a passive joint means for setting an adjustment angle of the base axis from an X axis parallel to the base linking unit.

20. The remote center of motion robotic system of claim 16, further comprising:
a third rotating joint means for coupling an end-effector to the end linking unit, wherein the kinematic means kinematically connects the first, second and third rotation joint means.

21. The remote center of motion robotic system of claim 20, further comprising:
an end-effector, the end-effector coupled to the end linking unit with the third rotating joint means.

22. The remote center of motion robotic system of claim 21, wherein
changing the angle between the base linking unit and the connecting linking unit allows an rcm end of the end-effector to rotate about a remote center of motion point.

23. The remote center of motion robotic system of claim 21, wherein the end-effector is coupled to the end linking unit in a position parallel to the connecting linking unit.

24. The remote center of motion robotic system of claim 20 wherein the kinematic means is at least one belt drive.

25. The remote center of motion robotic system of claim 20, further comprising:
a connecting unit rotating means coupled to the connecting linking unit to rotate the connecting linking unit around a first axis.

26. The remote center of motion robotic system of claim 25, further comprising:
a base unit rotating means coupled to the base rotating joint means for rotating the base unit around the base axis.

27. A remote center of motion robotic system comprising:
a base unit;
a base rotating joint means for connecting the base unit to a base and for allowing the base unit to rotate around a base axis with respect to the base;
a base unit rotating means coupled to the base rotating joint means for rotating the base unit around the base axis;
a base linking unit;
a pivot joint means for moveably coupling the base unit to the base linking unit;
a connecting linking unit;
a first rotating joint means for coupling the connecting linking unit to the base linking unit;
a connecting link rotating means for rotating the connecting link around a first rotation axis;
an end linking unit;
a second rotating joint means for coupling the end linking unit to the connecting linking unit;
an end-effector;
a third rotating joint means for connecting the end-effector to the end linking unit; and
a kinematic means for kinematically connecting the first, second and third rotating joint means.

* * * * *